(12) United States Patent
Westheim

(10) Patent No.: US 12,398,112 B2
(45) Date of Patent: Aug. 26, 2025

(54) CRYSTALLINE FORM OF OZANIMOD HYDROCHLORIDE

(71) Applicant: Synthon B.V., Nijmegen (NL)

(72) Inventor: Raymond Westheim, Nijmegen (NL)

(73) Assignee: Synthon B.V., Nijmegen (NL)

( * ) Notice: Subject to any disclaimer, the term of this patent is extended or adjusted under 35 U.S.C. 154(b) by 533 days.

(21) Appl. No.: 17/995,180

(22) PCT Filed: Mar. 17, 2021

(86) PCT No.: PCT/EP2021/056821
§ 371 (c)(1),
(2) Date: Sep. 30, 2022

(87) PCT Pub. No.: WO2021/197852
PCT Pub. Date: Oct. 7, 2021

(65) Prior Publication Data
US 2023/0183194 A1    Jun. 15, 2023

(30) Foreign Application Priority Data
Apr. 2, 2020 (EP) .................................. 20167780

(51) Int. Cl.
*C07D 271/06* (2006.01)
(52) U.S. Cl.
CPC ........ *C07D 271/06* (2013.01); *C07B 2200/13* (2013.01)

(58) Field of Classification Search
CPC ................................................... C07D 271/06
See application file for complete search history.

(56) References Cited

U.S. PATENT DOCUMENTS

| | | |
|---|---|---|
| 2019/0248755 A1 | 8/2019 | Chen et al. |
| 2019/0337908 A1 | 11/2019 | Chen et al. |
| 2020/0339524 A1 | 10/2020 | Chen et al. |

FOREIGN PATENT DOCUMENTS

| | | |
|---|---|---|
| EP | 3470400 | 6/2017 |
| EP | 3508481 | 9/2017 |
| WO | WO2011060392 | 5/2011 |
| WO | WO2017215617 | 12/2017 |
| WO | WO2018050091 | 3/2018 |
| WO | WO2018215807 | 11/2018 |
| WO | WO2019042219 | 3/2019 |

OTHER PUBLICATIONS

A. Rescaglio et al., "Tribo-electrification of pharmaceutical powder blends," *Particulate Science and Technology*, vol. 37, No. 8, Nov. 17, 2019, pp. 1024-1031.

*Primary Examiner* — Shawquia Jackson
(74) *Attorney, Agent, or Firm* — Buscher Patent PLLC

(57) ABSTRACT

The presented invention relates to crystalline form, Form A of Ozanimod hydrochloride, processes for preparation thereof and pharmaceutical compositions comprising the Ozanimod hydrochloride Form A.

12 Claims, 4 Drawing Sheets

Figure 4

Glass container with non-electrostatic crystals of Form A of Ozanimod hydrochloride:

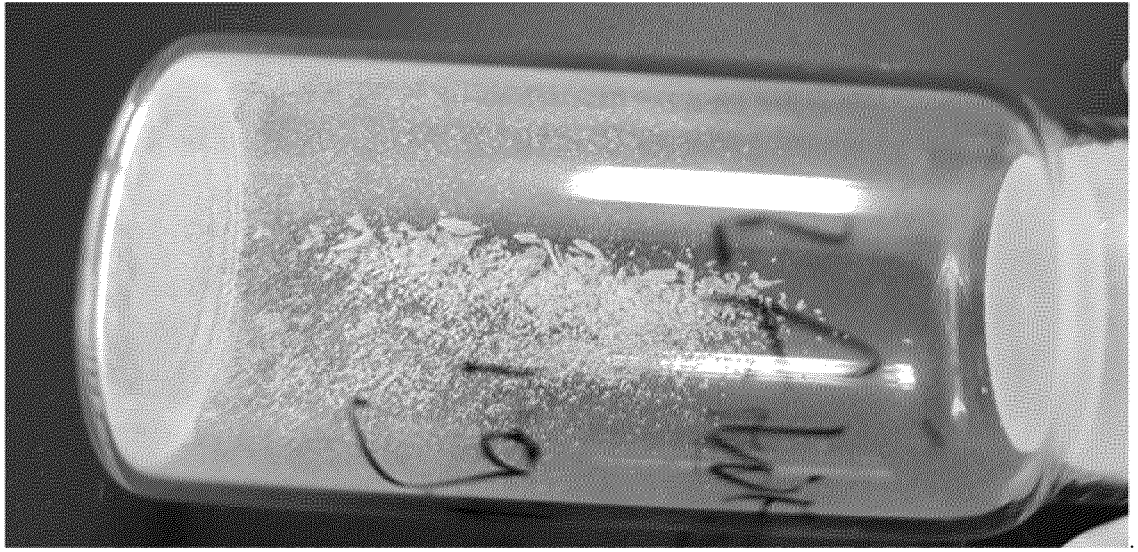

This picture is taken from above and slightly to the side, the crystals are clearly at the bottom of the glass container.

Glass container with big lumps of electrostatic crystals of Form CS1 of Ozanimod hydrochloride:

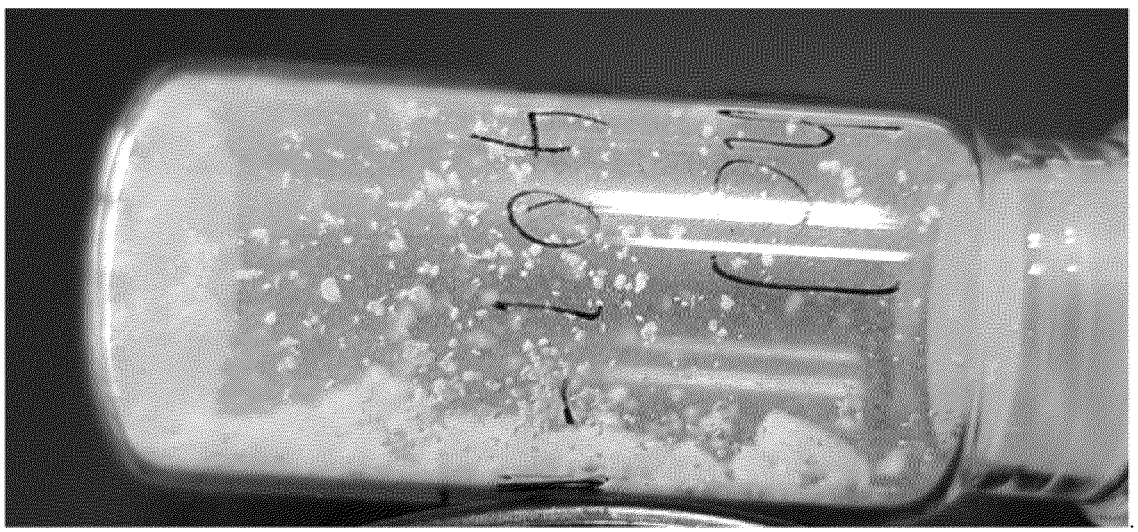

This picture is taken from above and slightly to the side, the crystals are clearly sticking to all sides of the glass container.

CRYSTALLINE FORM OF OZANIMOD HYDROCHLORIDE

The invention relates to crystalline form of Ozanimod hydrochloride, compound of formula (1), to processes for preparation thereof and to pharmaceutical compositions comprising the crystalline form of Ozanimod hydrochloride.

BACKGROUND OF THE PRESENT INVENTION

This invention relates to crystalline form of Ozanimod hydrochloride, compound of formula (1), to processes for preparation thereof and to pharmaceutical compositions comprising the crystalline form of Ozanimod hydrochloride;

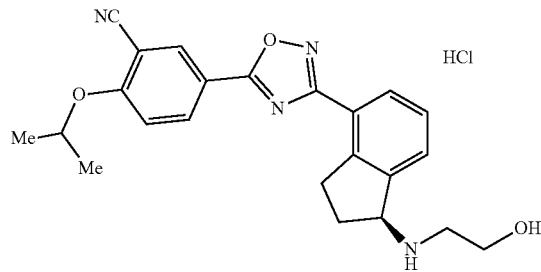

(1)

Ozanimod, 5-[3-[1(S)-(2-Hydroxyethylamino)-2,3-dihydro-1H-inden-4-yl]-1,2,4-oxadiazol-5-yl]-2-isopropoxy-benzonitrile, is an oral agonist of the lysophospholipid S1P1 and S1P5 receptors. Ozanimod has been registered for the treatment for patients with relapsing multiple sclerosis and it is expected to be further registered also for the treatment of ulcerative colitis and for the treatment of Crohn's disease.

Ozanimod and its pharmaceutically acceptable salts, including the hydrochloride salt, were first described in patent application WO2011060392. Crystalline forms of Ozanimod hydrochloride have also been described in the prior art. WO2017215617 describes polymorphic form CS1, WO2019042219 describes polymorphic form CS2 and WO2018050091 describes polymorphic form CS3.

The known crystalline forms of Ozanimod hydrochloride have the tendency to be electrostatic, easily adhering on surfaces.

Powdered material electrostatically charged causes flow problems during industrial production reducing quality and productivity of the process and leading to inferior products and higher costs.

By the reason of the foregoing, it has been desirable to provide a stable polymorphic form of Ozanimod hydrochloride with improved flow properties to further use in pharmaceutical compositions.

We have found a crystal form, Form A of Ozanimod hydrochloride. Crystalline Form A of Ozanimod hydrochloride has improved flow properties and it is advantageous to be used in the industrial scale production and in pharmaceutical compositions.

BRIEF DESCRIPTION OF THE INVENTION

The presented invention relates to crystalline form, Form A of Ozanimod hydrochloride, compound of formula (1) and processes for preparation thereof;

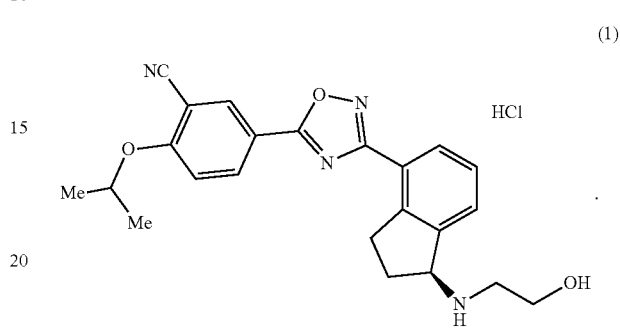

(1)

The presented invention further relates to pharmaceutical compositions comprising the crystalline form, Form A of Ozanimod hydrochloride.

Form A of Ozanimod hydrochloride, of the presented invention has improved flow properties and has good stability.

BRIEF DESCRIPTION OF THE DRAWINGS

FIG. 4 depicts a glass container with crystals of Form A of Ozanimod hydrochloride, prepared according to Example 1 and a glass container with crystals of Form CS1 of Ozanimod hydrochloride, prepared according WO2017215617.

DETAILED DESCRIPTION OF THE INVENTION

The presented invention relates to crystalline form, Form A of Ozanimod hydrochloride, compound of formula (1), processes for preparation thereof and pharmaceutical compositions comprising it.

The crystalline form, Form A can be characterized by XRPD pattern having 2θ values 7.9°, 11.8°, 13.9°, 15.2°, 19.8° and 23.4° degrees 2 theta (±0.2 degrees 2 theta). The crystalline form, Form A can be further characterized by XRPD pattern described in the following table:

| Angle 2-Theta ° | Intensity % | Angle 2-Theta ° | Intensity % | Angle 2-Theta ° | Intensity % | Angle 2-Theta ° | Intensity % |
|---|---|---|---|---|---|---|---|
| 3.99 | 100.00 | 15.88 | 28.42 | 22.90 | 42.49 | 31.81 | 18.31 |
| 5.28 | 18.49 | 16.11 | 26.98 | 23.46 | 47.46 | 32.73 | 15.20 |
| 6.59 | 16.77 | 16.86 | 35.31 | 23.81 | 43.74 | | |
| 7.94 | 60.00 | 17.28 | 39.49 | 24.50 | 65.34 | | |
| 11.89 | 37.79 | 18.08 | 33.77 | 25.26 | 54.47 | | |

-continued

| Angle 2-Theta ° | Intensity % | Angle 2-Theta ° | Intensity % | Angle 2-Theta ° | Intensity % | Angle 2-Theta ° | Intensity % |
|---|---|---|---|---|---|---|---|
| 12.72 | 73.85 | 18.94 | 43.32 | 26.30 | 41.51 | | |
| 13.10 | 53.77 | 19.36 | 44.94 | 27.46 | 33.00 | | |
| 13.39 | 43.92 | 19.86 | 82.21 | 27.87 | 31.96 | | |
| 13.94 | 78.02 | 20.91 | 45.95 | 29.07 | 29.61 | | |
| 14.38 | 46.68 | 21.28 | 57.65 | 30.25 | 24.23 | | |
| 15.21 | 46.16 | 21.85 | 33.53 | 31.50 | 19.59 | | |

Figure 1:
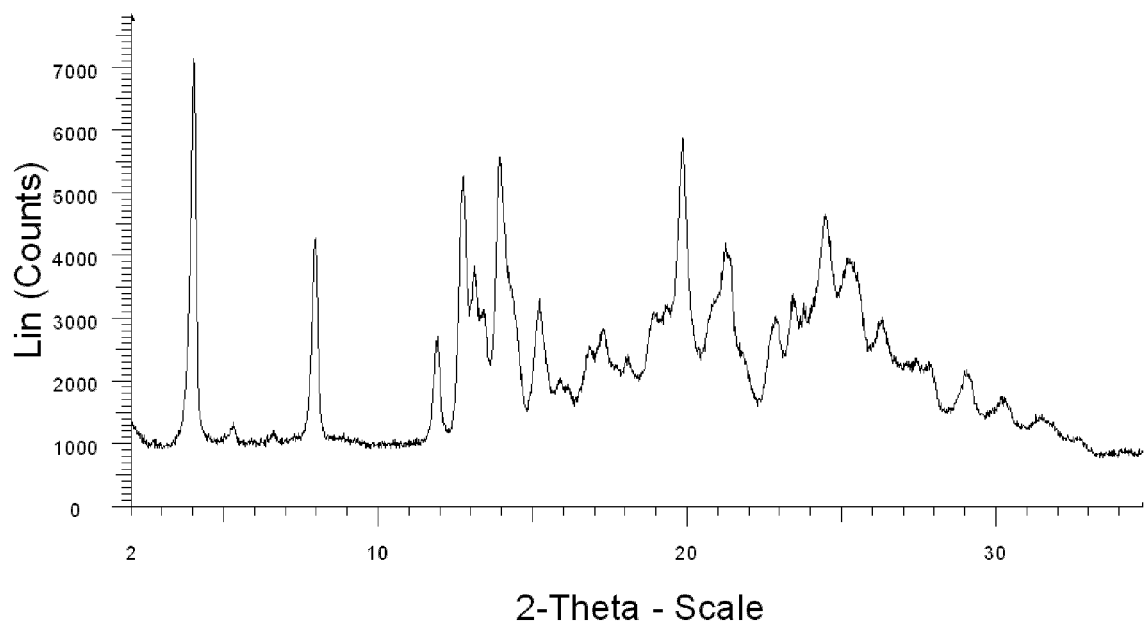
FIG. 1 depicts the X-Ray Powder Diffractogram (XRPD) of Form A of Ozanimod hydrochloride prepared according to Example 1.

The crystalline form, Form A can be also characterized by XRPD pattern depicted in FIG. 1.

Figure 2:
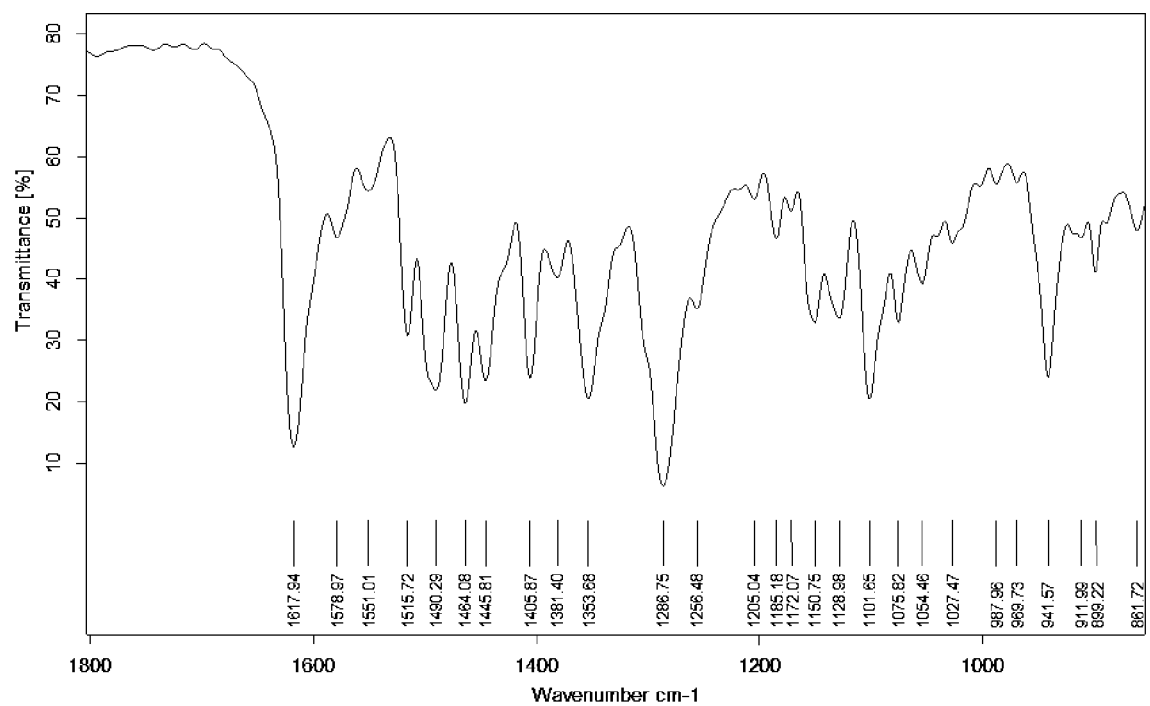
FIG. 2 depicts the infrared absorption spectrum in potassium bromide of Form A of Ozanimod hydrochloride prepared according to Example 1.

The crystalline form, Form A can be also characterized by the infrared absorption spectrum in potassium bromide depicted in FIG. 2. Form A exhibit a characteristic absorption band at a wavenumber of 1490.2±2.5 cm$^{-1}$.

Surprisingly, the crystals of Form A of Ozanimod hydrochloride, differently from the known crystals of Ozanimod hydrochloride (e.g. Form CS1 prepared according to WO2017215617); are not electrostatically charged and they do not adhere on surfaces as depicted in FIG. 4.

The crystalline Form A of the present invention is in "substantially pure" crystalline form. The term "substantially pure" as used herein includes reference to crystalline forms of, or greater than, 70%, preferably 80%, more preferably 90%, more preferably 95%, more preferably 97%, more preferably 98%, more preferably 99% or more polymorphic purity as determined, for example, by X-ray powder diffraction.

Typically, in order for a sample of Ozanimod hydrochloride Form A to have an XRPD pattern that substantially corresponds to FIG. 1, the Form A sample must be in a (chemically) pure form (typically at least 90% pure) and in a polymorphically pure form (typically at least 90% polymorphically pure).

The crystalline form, Form A can be prepared by a process comprising:
  a. Dissolving of compound of formula (1) in a mixture of water and a propanol alcohol to obtain a solution;
  b. Isolating the solid form by cooling to a temperature between 15° C. and 25° C.

The suitable propanol alcohol can be selected from 1-propanol or 2-propanol or a mixture thereof preferably, the propanol alcohol is 2-propanol.

The ratio (vol:vol) between the water and propanol alcohol can be between 2:1 and 7:1, preferably it is between 3:1 and 5:1, more preferably it is 4:1.

In the process for the preparation of the crystalline form, Form A, Ozanimod hydrochloride can be first dissolved in a mixture of water and propanol alcohol at a temperature between 20° C. to 30° C. followed by heating to a temperature between 70° C. and 110° C., preferably between 70° C. and 100° C.

Figure 3:
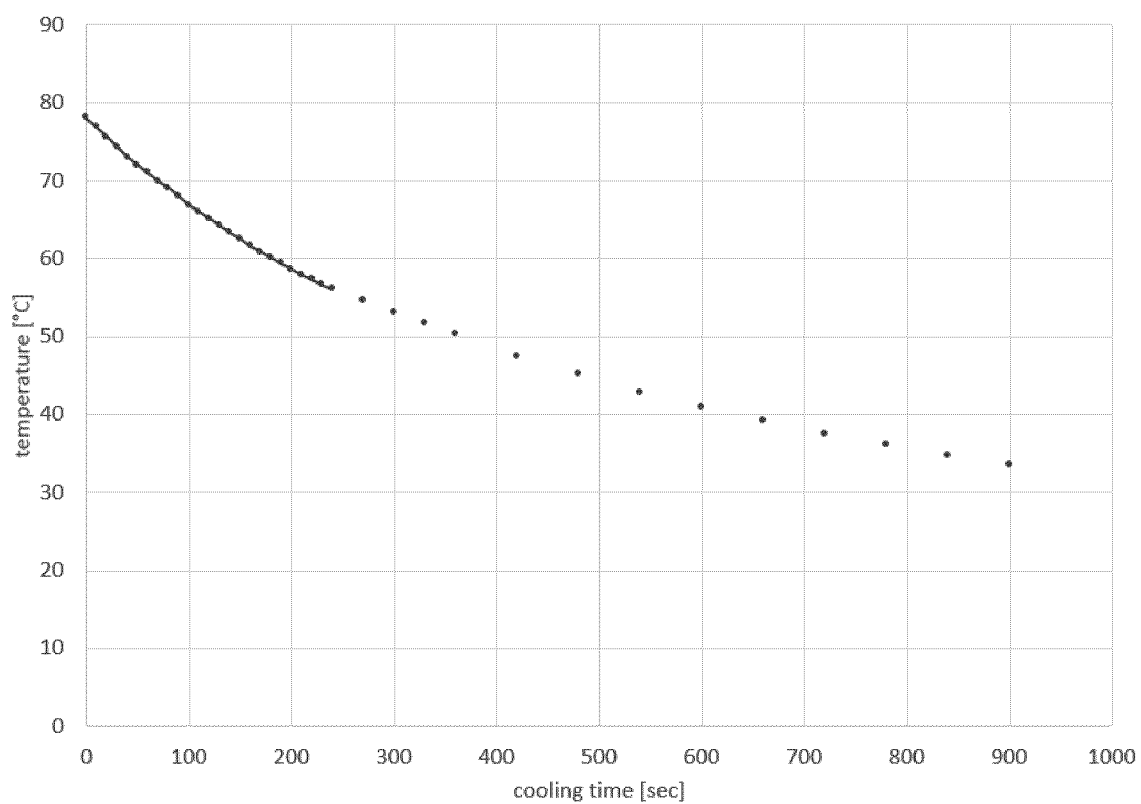
FIG. 3 depicts the cooling curve in the crystallization process of Form A of Ozanimod hydrochloride prepared according to Example 1.

After obtaining a clear solution, the solution can be cooled to a temperature between 15° C. to 25° C. As known in the art, the cooling speed may influence the polymorphic crystallization process; Form A of Ozanimod hydrochloride may be obtained by cooling from 80° C. to 33.5° C. in a range of 10 to 30 minutes, preferably in a range of 10 to 25 minutes, more preferably in 15 minutes following the curve as depicted in FIG. 3.

During cooling the solid formation is allowed. The solid can be isolated using any suitable technique, preferably the solid is isolated by filtration. The solid can be dried using technique known to the skilled person in the art, preferably the solid is dried by air.

The crystalline form, Form A of Ozanimod hydrochloride showed to be stable and to have good flowability which is advantageous in particular in industrial scale production.

The crystalline form, Form A of Ozanimod hydrochloride of the present invention can be processed into a suitable pharmaceutical composition. The solid form can be mixed in the pharmaceutical composition with pharmaceutically acceptable adjuvants, diluents or carriers. The amount of crystalline form, Form A in the composition depends on the condition and a patient to be treated. The pharmaceutical composition can be in form of oral emulsion, solution, suspension, syrup or solid oral composition, for example a capsule, a tablet, a powder, a granule or a dragee. Preferably the pharmaceutical composition is in the form of a solution or a capsule. The crystalline form, Form A according to the present invention can be mixed in the composition with one or more additives known to those skilled in the art such as diluent(s), filler(s), extender(s), binder(s), wetting agent(s), disintegrating agent(s), absorbent(s), lubricant(s), buffering agent(s), emulsifying agent(s), suspending agent(s), sweetening agent(s) and flavouring agent(s). Preferably, the crystalline form, Form A is mixed with filler(s), disintegrating agent(s) and lubricant(s). The solid oral composition can be coated with a coating.

The suitable pharmaceutical composition can be in a parenteral form such as an injection, infusion, injectable depot or in a liposomal form comprising pharmaceutically acceptable aqueous or non-aqueous solution(s), dispersion(s) or emulsions. The pharmaceutical composition can be also in a form of a powder for reconstitution into an injection or infusion.

The crystalline form, Form A or a pharmaceutical composition comprising the crystalline Form A can be used in therapy, preferably for the treatment of conditions treatable with Ozanimod hydrochloride such as the treatment of relapsing-remitting multiple sclerosis or ulcerative colitis or Crohn's disease. A patient can be treated for relapsing-remitting multiple sclerosis or ulcerative colitis or Crohn's disease, administering, a pharmacologically effective dose of the crystalline form A or a pharmacologically effective dose of a pharmaceutical composition comprising the crystalline Form A.

EXAMPLES

XRPD spectrum was obtained using the following measurement conditions.

Panalytical Empyrean diffractometer with θ-2θ geometry (transmition mode), equipped with a PixCell 3D detector;

| Start angle (2θ): | 2.0° |
|---|---|
| End angle (2θ): | 35.0° |
| Step size: | 0.013° |
| Scan speed: | 0.0095°/seconds |
| Radiation type: | Cu |
| Radiation wavelengths: | 1.5406 Å (Kα) |
| Divergence slit: | 1/2° |
| Antiscatter slit: | 2° |
| Soller slit: | 0.02 rad |
| Detector slit: | 8 mm |

Infrared absorption spectrum was obtained according to the potassium bromide tablet method in the infrared absorption spectrum measurement method as described in the Japanese Pharmacopoeia, General Tests by using FT/IR-620 (JASCO Corporation) with a measurement range of 850-4000 $cm^{-1}$ (FIG. 2 shows the range 850-1800 $cm^{-1}$).

Example 1: Preparation of Crystalline Form A of Ozanimod Hydrochloride

Ozanimod hydrochloride was prepared according to a process disclosed in WO2011060392 application.

0.5 g of Ozanimod hydrochloride was suspended in 5 ml of water/2-propanol (4:1 V/V) at 25° C. The suspension was heated to reflux. A clear solution was obtained. The solution was allowed to cool to 25° C. (from 80° C. to 33.5° C. in 15 minutes following the curve as described in FIG. 3) allowing the formation of the crystalline form A of Ozanimod hydrochloride. The mixture obtained was filtered over a P3-glass filter. Form A of Ozanimod hydrochloride was air-dried overnight at 25° C. A white to greyish hard solid in a quantitative yield was obtained. The solid was milled providing a powder. XRPD pattern of obtained powder corresponds to the XRPD pattern depicted in FIG. 1. Infrared absorption measurement of obtained powder corresponds to the infrared absorption curve depicted in FIG. 2.

The invention claimed is:
1. Crystalline form of compound of formula (1),

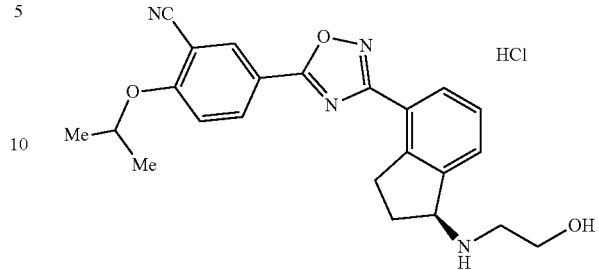

(1)

in Form A, characterized by XRPD pattern having 2θ values 7.9°, 11.8°, 13.9°, 15.2°, 19.8° and 23.4° degrees 2 theta (±0.2 degrees 2 theta).

2. Crystalline form according to claim 1 characterized by XRPD pattern depicted in FIG. 1.

3. Crystalline form according to claim 1 characterized by an absorption band at a wavenumber of 1490.2±2.5 $cm^{-1}$ in an infrared absorption spectrum in potassium bromide.

4. A process for preparation of the crystalline form according to claim 1 comprising:
 a) dissolving of compound of formula (1) in a mixture of water and a propanol alcohol to obtain a solution;
 b) isolating the solid form by cooling to a temperature between 15° C. and 25° C.

5. The process according to claim 4 wherein the propanol alcohol is selected form 1-propanol, 2-propanol or a mixture thereof.

6. The process according to claim 5 wherein the propanol alcohol is 2-propanol.

7. The process according to claim 4 wherein the ratio between water and the propanol alcohol is from 2:1 to 7:1.

8. The process according to claim 4 wherein the ratio between water and the propanol alcohol is 3:1 to 5:1.

9. The process according to claim 4 wherein the dissolution of step a) comprises heating to a temperature between 70° C. and 110° C.

10. A pharmaceutical composition comprising the crystalline form A according to claim 1.

11. A method for treating relapsing-remitting multiple sclerosis or ulcerative colitis or Crohn's disease, comprising administering to a patient, a pharmacologically effective dose of the crystalline form according to claim 1.

12. The process according to claim 9, wherein the dissolution of step a) comprises heating to a temperature between 70° C. and 100° C.

* * * * *